United States Patent [19]

Schack

[11] 4,430,514
[45] Feb. 7, 1984

[54] NOVEL METHOD FOR THE PREPARATION OF CF$_3$NF$_2$

[75] Inventor: Carl J. Schack, Chatsworth, Calif.

[73] Assignee: The United States of America as represented by the Secretary of the Navy, Washington, D.C.

[21] Appl. No.: 390,160

[22] Filed: Jun. 21, 1982

[51] Int. Cl.$^3$ .............................................. C07C 87/08
[52] U.S. Cl. .................................... 564/496; 564/118
[58] Field of Search ................................ 564/496, 118

[56] References Cited

U.S. PATENT DOCUMENTS 3,424,797  1/1969  Dybvig ............................... 564/118

Primary Examiner—Charles F. Warren
Assistant Examiner—Margaret B. Medley
Attorney, Agent, or Firm—R. F. Beers; K. E. Walden; J. C. LaPrade

[57] ABSTRACT

A novel method is provided for the preparation of difluoramino trifluoromethane by the direct fluorination of azidotrifluoromethane in the temperature range of 70° C. to 80° C. A potassium fluoride catalyst also may enhance the rate of reaction and increase the yield.

4 Claims, No Drawings

NOVEL METHOD FOR THE PREPARATION OF CF$_3$NF$_2$

BACKGROUND OF THE INVENTION

The known methods of synthesizing difluoramino trifluoromethane suffer from several serious deficiencies. Difluoroaminotrifluoromethane, CF$_3$NF$_2$, has been synthesized by numerous processes including the fluorination of amines, metal cyanides, nitriles and metal thiocyanates. Fluorinating agents that have been used include NF$_3$, N$_2$F$_4$, transition metal fluorides as well as fluorine. The principal drawbacks of all these processes is the formation of CF$_3$NF$_2$ in low yields accompanied by difficulty separable coproducts. For example many of the processes produce C$_2$F$_6$, that has a boiling point that is essentially the same as CF$_3$NF$_2$. It is therefore very difficult to effect their separation. In addition, nearly all of these processes suffer from poor reproducibility.

Other prior art processes, as disclosed by J. K. Ruff in Jour. of Organic Chemistry 32, p. 1675 (1967) require chromatographic purification of the product. Other prior art processes are disclosed in J. K. Ruff, Chem. Rev. Vol. 67 pg. 665 (1967), and in J. P. Freeman in *Advances in Fluorine Chem.* Vol. 6, pg. 287 (1970). These processes show low yields of difluoramino trifluoromethane.

SUMMARY OF THE INVENTION

The invention is a method for the direct fluorination of azidotrifluoromethane with gaseous fluorine at a temperature in the general range of 30° C. to 80° C. to produce difluoroamino trifluorometane A potassium fluoride catalyst may be used. The yield may exceed 70%, when the temperature is maintained in the range of 70° C. to 80° C. and a suitable catalyst is employed.

Accordingly, it is one object of the invention to provide a novel process for the preparation of difluoramino trifluoromethane.

DESCRIPTION OF THE PREFERRED EMBODIMENT

It has been discovered that the reaction of azidotrifluoromethane with fluorine is a reproducible, high yield process for the synthesis of difluoroamino trifluoromethane.

The equation is CF$_3$N$_3$+F$_2$→CF$_3$NF$_2$+N$_2$ Minimal side reactions are encountered.

The fluorine to be used in the example was scrubbed with NaF immediately before use.

The CF$_3$N$_3$ was produced according to the following equations

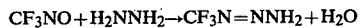

CF$_3$NO+H$_2$NNH$_2$→CF$_3$N=NNH$_2$+H$_2$O

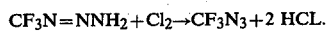

CF$_3$N=NNH$_2$+Cl$_2$→CF$_3$N$_3$+2 HCL.

The details of the preparation of the starting material is disclosed in an article entitled "Properties of Azido-trifluormethane" Inorgan Chem 1981, 20 pg. 2566-25-70—Karl O. Christe and Carl J. Schack.

This publication is incorporated herein by reference.

Synthesis of CF$_3$NF$_2$

A 30 ml stainless-steel Hoke cylinder was loaded with CF$_3$N$_3$ (1.68 mmol) and F$_2$ (6.70 mmol) at −196° C. The cooling bath was removed and as soon as the cylinder was free of frost, it was placed in an oven preheated to 70° C. After 24 hours the reactor was cooled to −196° C. and all volatile material, consisting mainly of the excess F$_2$ and by-product N$_2$, was pumped away. The condensable material (1.69 mmol) was shown by infrared spectroscopy and gas chromatographic analysis at 65° C. to be 51% unreacted CF$_3$N$_3$ and 49% CF$_3$NF$_2$ with a trace of CF$_4$. When fluorinated for an additional 24 hour period at 70° C., the yield of CF$_3$NF$_2$ was 84% and about 15% CF$_3$N$_3$ was still recovered. Further fluorination consumed the azide and produced CF$_3$NF$_2$ (92%), CF$_4$ (6%) and C$_2$F$_6$ (1–2%). A similar 70° C. fluorination reaction in which the reactor contained 18 mmol of anhydrous KF powder, gave a 68% yield of CF$_3$NF$_2$ after 1 day. After 2 days this yield had increased to 73% and was accompanied by a 6.4% yield of the degradation product CF$_4$.

Catalyst

The rate of reaction and overall yield is significantly increased by the use of a potassium fluoride catalyst. Another reaction that is run at temperatures higher than 80° C. or in the presence of CsF leads to further fluorination according to this equation

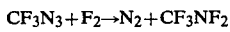

$$CF_3N_3 + F_2 \rightarrow N_2 + CF_3NF_2$$

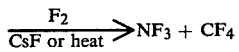

$$\xrightarrow[\text{CsF or heat}]{F_2} NF_3 + CF_4$$

The maximum yield of CF$_3$NF$_2$ observed in both catalyzed and uncatalyzed reactions for 1 day was about 70%. After slightly longer reaction times yields are in the 90–95% range. In addition to the by-products CF$_4$ and NF$_3$ which are easily separated, there was also some C$_2$F$_6$ formed (∼1%) when all the CF$_3$N$_3$ had reacted. Although not a very fast reaction, this synthesis has the advantages of high yield, easy product purification, and reproducibility.

It will be obvious to those skilled in the art that any other modifications, substitutions, combinations and sub-combinations or ingredients, and procedures may be used within the scope and spirit of the invention, in addition to those specifically recited above. It is intended by the claims which follow to cover these and all other obvious alternatives and variations as broadly as the state of the art properly permits.

What is claimed is:

1. A process for the production of difluoramino trifluoromethane comprising
reacting azidotrifluoromethane with fluorine in equal molar quantities to produce difluoroamino trifluoromethane according to the equation $$CF_3N_3 + F_2 \rightarrow CF_3NF_2 + N_2.$$

2. The process of claim 1 where the temperature of the reaction is in the range of 70° C. to 80° C.

3. The process of claim 1 wherein the reaction is conducted in the presence of a catalyst.

4. The process of claim 3 wherein the catalyst is potassium fluoride.